US012564399B2

(12) United States Patent (10) Patent No.: US 12,564,399 B2
Dreyfuss et al. (45) Date of Patent: Mar. 3, 2026

(54) TENSIONABLE KNOTLESS SURGICAL TECHNIQUES

(71) Applicant: ARTHREX, INC., Naples, FL (US)

(72) Inventors: Peter J. Dreyfuss, Naples, FL (US);
Amr W. Elmaraghy, Missisuaga (CA);
Gautam P. Yagnik, Miami, FL (US);
Andrew C. Petry, Naples, FL (US)

(73) Assignee: ARTHREX, INC., Naples, FL (US)

( * ) Notice: Subject to any disclaimer, the term of this
patent is extended or adjusted under 35
U.S.C. 154(b) by 449 days.

(21) Appl. No.: 18/158,614

(22) Filed: Jan. 24, 2023

(65) Prior Publication Data

US 2024/0245398 A1 Jul. 25, 2024

(51) Int. Cl.
*A61B 17/06* (2006.01)
*A61B 17/04* (2006.01)

(52) U.S. Cl.
CPC .................. *A61B 17/06166* (2013.01); *A61B 2017/0496* (2013.01)

(58) Field of Classification Search
CPC .............. A61B 17/06166; A61B 17/82; A61B 2017/06176; A61B 2017/0618; A61B 2017/06185
See application file for complete search history.

(56) References Cited

U.S. PATENT DOCUMENTS

| | | | |
|---|---|---|---|
| 5,123,913 A * | 6/1992 | Wilk ................ A61B 17/12009 |
| | | | 24/17 AP |
| 5,178,629 A * | 1/1993 | Kammerer ......... A61B 17/0469 |
| | | | 606/224 |
| 5,893,880 A | 4/1999 | Egan et al. |
| 6,077,277 A | 6/2000 | Mollenauer et al. |
| 8,876,865 B2 | 11/2014 | Goraltchouk et al. |
| 9,351,719 B2 | 5/2016 | McClellan et al. |
| 9,775,928 B2 * | 10/2017 | Ostapoff ................. A61L 17/10 |
| 10,448,944 B2 * | 10/2019 | Marchand .......... A61B 17/0401 |
| 10,492,780 B2 | 12/2019 | Gross et al. |
| 11,006,989 B2 | 5/2021 | Dooney et al. |
| 11,172,926 B1 | 11/2021 | Moliver |
| 11,272,924 B2 | 3/2022 | Crook et al. |
| 2007/0027475 A1 * | 2/2007 | Pagedas ........... A61B 17/06166 |
| | | | 606/228 |

(Continued)

FOREIGN PATENT DOCUMENTS

CN 114206231 A 3/2022

OTHER PUBLICATIONS

Denard et al., "A Tensionable Method for Subscapularis Repair after Shoulder Arthroplasty", Science Direct, Aug. 2018.

(Continued)

*Primary Examiner* — Alexander J Orkin
(74) *Attorney, Agent, or Firm* — Carlson, Gaskey & Olds, P.C.

(57) ABSTRACT

Methods for tissue repairs with surgical constructs having cinch loops and stoppers that do not require tying of knots are disclosed. A surgical construct includes a loop with a racking hitch terminating in a single tail. Mechanical pressure is applied to the single tail to deform an area of the surgical construct and form a bulge that acts as a stopper. A ferrule with internal features can be attached to a cerclage construct adjacent a racking hitch to act as a stopper and prevent the cerclage construct from loosening.

19 Claims, 3 Drawing Sheets

(56)                    References Cited

U.S. PATENT DOCUMENTS

| | | | |
|---|---|---|---|
| 2007/0179529 A1* | 8/2007 | Doyle | A61B 17/06166 |
| | | | 606/228 |
| 2007/0219587 A1* | 9/2007 | Accardo | A61B 17/06166 |
| | | | 606/228 |
| 2008/0065114 A1* | 3/2008 | Stone | A61B 17/0401 |
| | | | 606/279 |
| 2009/0259251 A1 | 10/2009 | Cohen | |
| 2009/0318961 A1* | 12/2009 | Stone | A61B 17/0401 |
| | | | 606/228 |
| 2010/0274282 A1* | 10/2010 | Olson | A61B 17/06166 |
| | | | 87/8 |
| 2011/0282384 A1* | 11/2011 | Odermatt | A61B 17/06166 |
| | | | 606/228 |
| 2013/0289564 A1* | 10/2013 | Bernstein | A61B 17/82 |
| | | | 606/74 |
| 2015/0032155 A1* | 1/2015 | Dreyfuss | A61B 17/06166 |
| | | | 606/228 |
| 2015/0051642 A1* | 2/2015 | Broom | A61L 31/14 |
| | | | 606/228 |
| 2017/0156727 A1* | 6/2017 | Wilson-Wirth | A61L 17/105 |
| 2018/0221022 A1* | 8/2018 | Choe | A61B 17/0487 |
| 2019/0175170 A1 | 6/2019 | Yagnik et al. | |
| 2020/0022701 A1* | 1/2020 | Crook | A61B 17/06166 |
| 2022/0378486 A1 | 12/2022 | Holowecky et al. | |

OTHER PUBLICATIONS

Hawi et al., "The Simple Cow Hitch Stitch Technique for Arthroscopic Rotator Cuff Repair and Stabilization Using Knotless Suture Anchors", Arthroscopy Associate of North America, 2015.
Unknown, "The SutureWeld"Osteoweld Health Technology.

* cited by examiner

TENSIONABLE KNOTLESS SURGICAL TECHNIQUES

BACKGROUND

The disclosure relates to the field of surgery and, more specifically, to tensionable knotless surgical constructs and associated knotless surgical techniques.

SUMMARY

Surgical constructs and tissue repairs are disclosed. A surgical construct can create a knotless, tensionable, self-locking repair without the need to tie any knots. A surgical construct can include (i) a loop; (ii) a loop interconnection; and (iii) a locking mechanism. A surgical construct can be a suturing construct. A surgical construct can be a cerclage construct.

A loop of a surgical construct can be a closed, flexible, continuous suture loop. A loop of a surgical construct can be a cerclage loop. A loop interconnection can be in the form of an interconnecting loop link such as a racking hitch or half hitch. A loop interconnection can be located between a loop and a locking mechanism. A locking mechanism can be a stopper. A stopper can be a suture bulge or deformation formed by applying mechanical pressure to a suture construct. A stopper can be a ferrule with internal features that allow one way tensioning of a cerclage construct.

A surgical construct can be employed to re-attach anatomical structures, for example, a first tissue to a second tissue, such as bone to bone, soft tissue, tendon, ligament, and/or bone, to each other and/or any combination of one another, by employing a self-locking, knotless, tensionable mechanism. A self-locking construct can be employed as a stand-alone construct or with additional fixation devices, for example, attached to one or more fixation devices.

Methods of knotless, tensionable surgical repairs are also disclosed. In an embodiment, a portion of a flexible strand can be deformed by applying mechanical pressure and/or compression to form at least one bulge or deformation adjacent a racking hitch. The at least one bulge or deformation creates obstruction of sutures loosening through a racking hitch type of knot. The suturing technique eliminates tying knots.

In another embodiment, a ferrule with internal features is attached to a cerclage repair adjacent a cerclage locking mechanism, to tension the cerclage repair and lock down the cerclage material. A cerclage locking mechanism can be an interconnecting cerclage loop link such as a racking hitch or half hitch.

DETAILED DESCRIPTION

Figure 1:
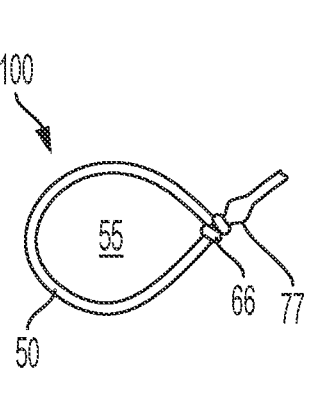
FIG. 1 illustrates a surgical construct employed in tissue repair according to an exemplary embodiment.
Figure 2:
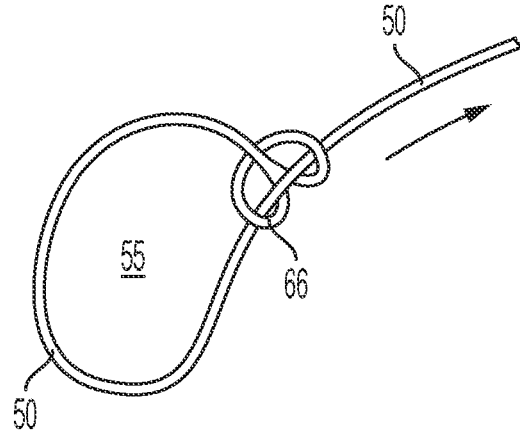
FIGS. 2-4 illustrate schematic steps of forming the surgical construct of FIG. 1.

Surgical constructs, assemblies and methods for knotless fixation of tissue are disclosed.

A surgical construct can create a knotless, tensionable, self-locking repair. A surgical construct can include (i) a loop; (ii) a loop interconnection; and (iii) a locking mechanism. A surgical construct can be a suturing construct. A surgical construct can be a cerclage construct.

A suturing construct can include: (i) a closed, flexible, adjustable, continuous suture loop; (ii) an interconnecting loop link such as a racking hitch or half hitch; and (iii) a locking mechanism (a stopper). A stopper can be a suture bulge or deformation formed by applying mechanical pressure to the suturing construct. A suturing construct can consist essentially of suture. A suturing construct can consist essentially of a braid with a monofilament core. A suturing construct can be employed to attach or re-attach anatomical structures, for example, a first tissue to a second tissue, such as soft tissue, tendon, ligament, and/or bone, to each other and/or any combination of one another, by employing a self-locking, knotless mechanism. A suturing construct can be employed as a stand-alone construct or with additional fixation devices, for example, attached to one or more knotted or knotless suture anchors.

A cerclage construct can include: (i) a cerclage loop; (ii) an interconnecting cerclage loop link such as a racking hitch or half hitch; and (iii) a locking mechanism (a stopper). A stopper can be a ferrule with internal features that allow one way tensioning of the cerclage construct. A cerclage construct can consist essentially of cerclage suture. A cerclage construct can consist essentially of cerclage suture tape. A cerclage construct can be employed to re-attach anatomical structures, for example, bone to bone. A cerclage construct can be employed as a stand-alone construct or with additional fixation devices, for example, attached to one or more fixation devices such as bone plates, screws and/or implants.

Methods of surgical repairs are also disclosed. An exemplary method includes inter alia the steps of (i) passing a flexible construct through and/or around tissue to be repaired; (ii) passing a tail of the flexible construct through a loop of the flexible construct to form a cinch; and (iii) stopping the flexible construct from loosening by forming a locking mechanism adjacent the cinch. The flexible construct can be a suturing construct. The flexible construct can be a bone cerclage construct.

In an exemplary embodiment, a portion of a suturing construct can be deformed by applying mechanical pressure and/or compression to form at least one bulge, enlargement, or deformation in the suture adjacent a racking hitch knot. The at least one bulge enlargement, or deformation creates obstruction of the sutures loosening through the racking hitch type of knot. The suturing technique eliminates tying knots. Tension is applied to the racking hitch and subsequently, mechanical pressure is applied to the suture. The mechanical pressure creates one or more monofilament bulges out and through the braid, which act as a stopper.

In another exemplary embodiment, a cerclage repair can be conducted with cerclage material (such as cerclage tape) secured by a racking hitch type of knot. A ferrule with internal features is slipped over ends of the cerclage tape and tensioned down to the hitch where it locks in a one-way manner. The hitch holds much of the tension of the repair, while the ferrule acts as a stopper.

Figure 12:
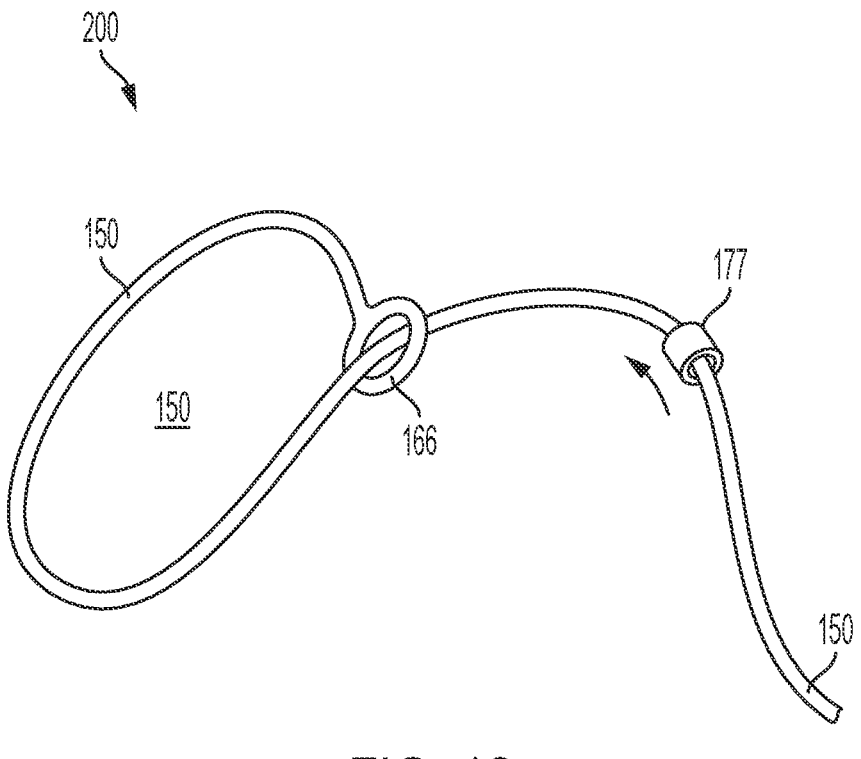
FIG. 12 illustrates a surgical construct employed in tissue repair according to another exemplary embodiment.
Figure 13:
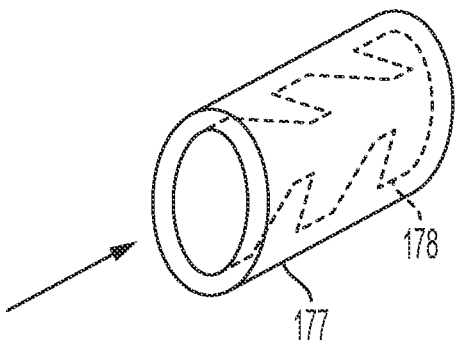
FIG. 13 is an enlarged view of a locking mechanism of the surgical construct of FIG. 12.

Referring now to the drawings, where like elements are designated by like reference numerals, FIGS. 1-12 illustrate surgical constructs 100, 200 employed in surgical tissue repairs according to exemplary embodiments. FIGS. 1-4 illustrate surgical construct 100 employed in a suturing repair according to an exemplary embodiment. FIGS. 5-11 illustrate subsequent steps of a tissue suturing repair 101 with the surgical construct 100 of FIG. 1. FIGS. 12 and 13 illustrate surgical construct 200 employed in bone cerclage repair according to another exemplary embodiment of the present disclosure.

Suturing construct 100 (surgical construct 100; suture 100; self-locking construct 100; knotless, tensionable construct 100; knotless closure suture 100; flexible construct 100; side-to-side knotless suture 100) is formed of a flexible strand 50 (flexible material 50, suture construct 50, suturing construct 50) employed for fixation of first tissue to second tissue. In an exemplary embodiment, suturing construct 100 is formed of flexible strand 50 which includes a central strand of core suture 10 (first strand or filament; inner strand) and an outer strand of suture 11 (second strand or filament; outer strand; coreless suture) covering the central strand. The central strand 10 can be a monofilament core. In an embodiment, the outer strand 11 covers completely the central strand 10 in at least two directions, a longitudinal direction and a transversal direction. Additional details of flexible strand 50 are shown in FIG. 4.

Figure 5:
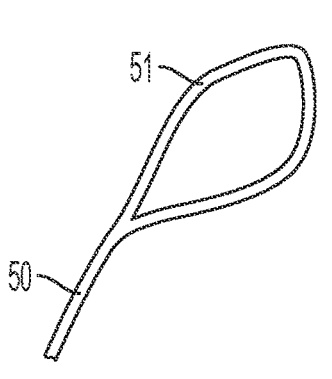
FIGS. 5-11 illustrate schematic subsequent steps of a tissue repair with the surgical construct of FIG. 1.
Figure 6:
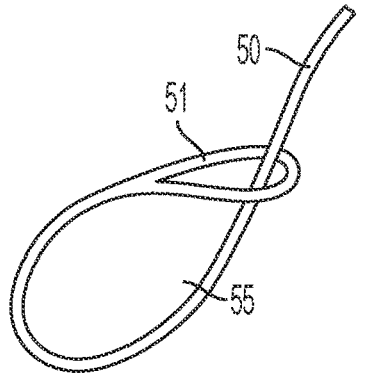
Figure 7:
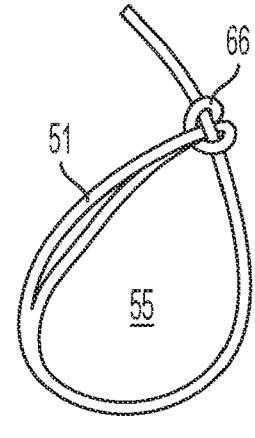
Figure 8:
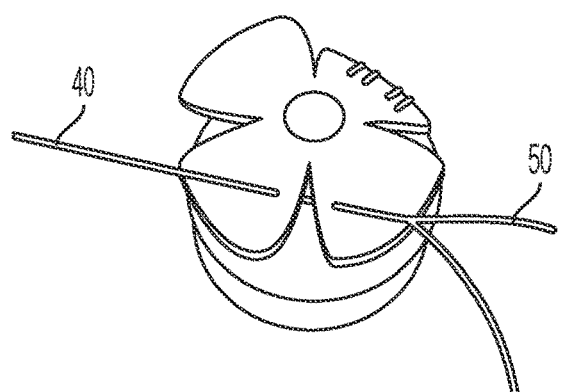

Suturing construct 100 also includes one or more loop interconnections 66 and one or more locking mechanisms 77 (stopping mechanism 77). In an embodiment, and as shown in FIGS. 5-7, suturing construct 100 is provided with a small loop 51 for creating racking hitch 66 (racking hitch knot 66; cinch 66; luggage tag 66; luggage tag stitch 66) and flexible, closed, adjustable, self-locking, tensionable loop 55. Small loop 51 may be formed integrally to, or separate from, the suturing construct. Loop 51 may be part of outer strand 11 or, alternatively, part of inner strand 10. In yet another embodiment, loop 51 may be part of both strands 10, 11. In additional embodiments, small loop 51 may be attached to the suturing construct (for example, to one or both of the outer and inner strands) by any methods known in the art. Small loop 51 can be integral to the flexible strand 50.

Figure 3:
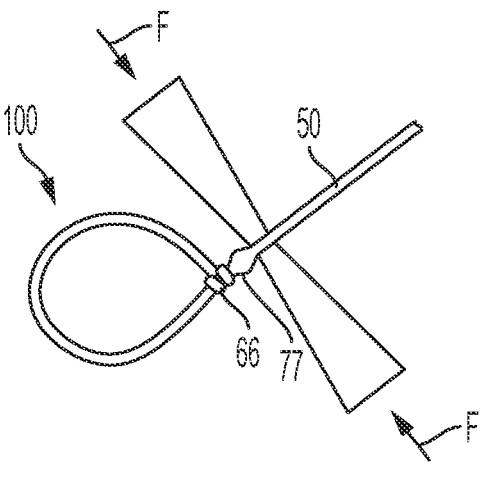
Figure 4A:
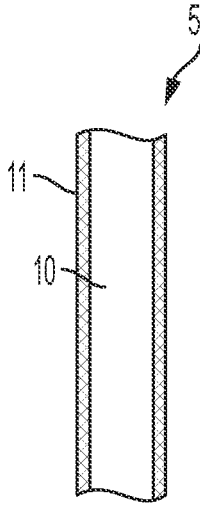
Figure 4B:
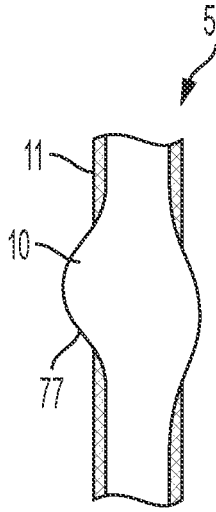

Reference is now made to FIGS. 3 and 4. Subsequent to the formation of loop interconnection 66, locking mechanism 77 is formed by applying mechanical pressure, compression, or force F to an area of the suturing construct 100 adjacent the loop interconnection 66, to form a smashed or crimped area 77 (stopping or locking mechanism 77) in the flexible strand 50. The locking mechanism 77 acts as a stopper. FIGS. 4(*a*) and 4(*b*) illustrate enlarged views of the strands 10, 11 before and after application of the mechanical pressure and compression. Bulge 77 of FIG. 4(*b*) is formed after the application of mechanical pressure or mechanical force to the flexible strand 50. When mechanical pressure is applied, the monofilament core 10 bulges out and through the braid 11 (the UHMWPE braid 11), piercing the braid 11 as clearly shown in FIG. 4(*b*). Bulge 77 can be any deformation, enlargement, expansion, protuberance, or flattened area/region of the flexible strand 50 with a size which does not allow movement or passage through the loop interconnection 66. The monofilament suture 11 with the solid core 10 can be flattened to distort its cross-sectional view and achieve a more oval cross-sectional view.

While bulge 77 locks the construct 100, it is important to note that bulge 77 acts primarily as a stopper for the suture, creating an obstruction of the suture loosening through the racking hitch type of knot 66. In this manner, without using any electrically powered sources of welding/deformation of the suture, the mechanical pressure alone eliminates tying of knots while providing a secure, reinforced locking of the suture 50.

Reference is now made to FIGS. 8-11 which illustrate a suturing repair 101 (FIG. 11) with exemplary surgical construct 100. Flexible strand 50 is passed through first tissue 90

(soft tissue 90) attached to second tissue 80 (bone 80) with a suturing instrument 40, for example, needle 40.

Figure 9:
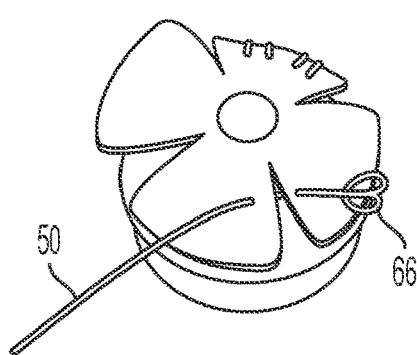
Figure 10:
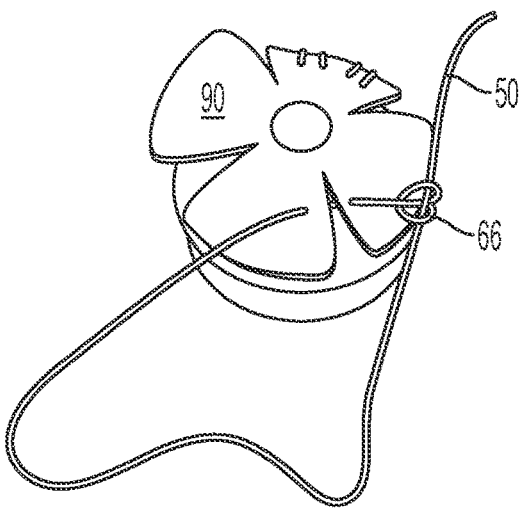
Figure 11:
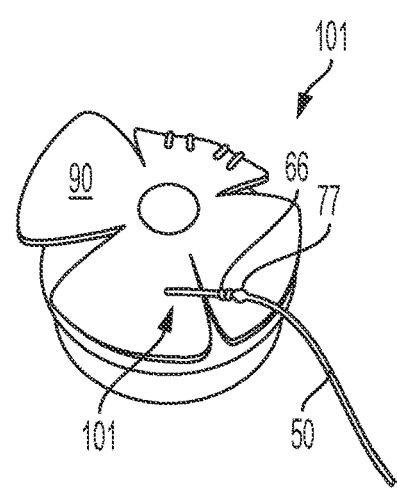

FIGS. 9 and 10 illustrate the formation of loop interconnection 66 (racking hitch knot 66) and passing of single tail of flexible strand 50 through the racking hitch knot 66. Tension is applied by pulling on the single tail of flexible strand 50 to tension the construct. Mechanical force and/or pressure and/or compression is applied to a region of the flexible strand 50 adjacent the loop interconnection 66 to form stopping/locking mechanism 77 (bulge or deformation 77) in the strand 50.

Final repair 101 includes suturing construct 100 with bulge or enlargement 77 formed in the flexible strand 50 by applying mechanical pressure and locked into place by racking hitch 66, unable to slip or slide out of the loop formed around first tissue 90 (for example, soft tissue 90) attached to second tissue 80 (for example, bone 80).

Flexible strand 50 (suturing construct 50) can include a single filament, or fiber, or can include multiple continuous filaments, segments or regions of filaments that have different configurations (for example, different diameters and/or different compositions) and allow formation of at least one bugle 77 by application of mechanical pressure and/or compression.

Flexible strand 50 can be made of any known suture construct, such as multifilament, braided, knitted, woven suture, or including fibers of ultrahigh molecular weight polyethylene (UHMWPE) or the FiberWire® suture (disclosed in U.S. Pat. No. 6,716,234, the disclosure of which is hereby incorporated by reference in its entirety herein). The flexible strand can be also formed of suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein.

FIGS. 12 and 13 illustrate schematic views of surgical construct 200 of the present disclosure. Surgical construct 200 of FIG. 12 is about similar to surgical construct 100 detailed above in that it is also a knotless, tensionable, self-locking construct that includes a loop 150 with one or more loop interconnections 166 such as a racking hitch knot 166 and one or more stopping/locking mechanisms 177. However, surgical construct 200 differs from construct 100 in that (i) surgical construct 200 is a cerclage construct with flexible strand 150 formed of cerclage materials such as metals and/or tapes such as suture tape, among others; and (ii) surgical construct 200 includes a ferrule 177 or collet 177 with internal features 178 forming stopping/locking mechanism.

A cerclage repair with cinch 166 (racking hitch 166) is created around bone 80 and/or tissue 90. Ferrule 177 has internal features 178 that permit one way tensioning and one way suture direction and movement. Ferrule 177 slipped over the ends of the flexible strand 150 (cerclage tape 150) is tensioned down to the hitch 166 where it locks in a one-way manner. The hitch 166 holds much of the tension of the cerclage repair while the ferrule 166 acts as a stopper. The cerclage repair of the present disclosure is tensionable and knotless in that it eliminates tying knots from suturing techniques such as cerclage and side-to-side repairs. With the racking hitch geometry of the cerclage technique disclosed above, the ferrule 177 no longer needs to hold the entire force of the repair, but instead acts as a stopper. This aspect alone provides additional strength to the overall cerclage repair.

A suturing construct 100 can include: (i) a closed, flexible, adjustable, continuous suture loop 55; (ii) an interconnecting loop link 66 such as a racking hitch 66 or half hitch 66 or cinch 66; and (iii) a locking mechanism 77 or stopper 77. A stopper 77 can be a suture bulge or deformation formed by applying mechanical pressure to the suturing construct. A suturing construct 100 can consist essentially of suture 50. A suturing construct 100 can consist essentially of a braid 11 with a monofilament core 10. A suturing construct 10 can be employed to attach or re-attach anatomical structures, for example, a first tissue 90 to a second tissue 80, such as soft tissue, tendon, ligament, and/or bone, to each other and/or any combination of one another, by employing a self-locking, knotless mechanism. A suturing construct 100 can be employed as a stand-alone construct or with additional fixation devices, for example, attached to one or more fixation devices.

A cerclage construct 200 can include: (i) a cerclage loop 150; (ii) an interconnecting cerclage loop link 166 such as a racking hitch 166 or half hitch 166 or cinch 166; and (iii) a locking mechanism 177 or stopper 177. A stopper 177 can be a ferrule 177 provided with internal features 178 that allow one way tensioning of a cerclage construct. A cerclage construct 200 can consist essentially of suture tape 150. A cerclage construct 200 can be employed to re-attach anatomical structures, for example, bone to bone, or bone to soft tissue. A cerclage construct 200 can be employed as a stand-alone construct or with additional fixation devices, for example, attached to one or more fixation devices such as bone plates, anchors, screws and/or implants.

Flexible strands 50, 150 may be in the form of any elongated members, fibers, or materials, or combinations thereof. Flexible strands 50, 150 may be coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the suture, loop security, pliability, handleability or abrasion resistance, for example.

Flexible strands 50, 150 can be made of any known suture construct, such as multifilament, braided, knitted, woven suture, or including fibers of ultrahigh molecular weight polyethylene (UHMWPE) or the FiberWire® suture (disclosed in U.S. Pat. No. 6,716,234, the disclosure of which is hereby incorporated by reference in its entirety herein). Flexible strands 50, 150 can be also formed of suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein.

Flexible strands 50, 150 can be also provided with tinted tracing strands, or otherwise contrast visually with other areas/regions of the construct, which remains a plain, solid color, or displays a different tracing pattern, for example. Various structural elements of flexible strands 50, 150 such as loops 55, 155 and/or tails may be visually coded, making identification and handling of the suture loops and ends simpler. Easy identification of suture in situ is advantageous in surgical procedures.

The term "high strength suture" is defined as any elongated flexible member, the choice of material and size being dependent upon the particular application. For the purposes of illustration and without limitation, the term "suture" as used herein may be a cable, filament, tape, thread, wire, fabric, or any other flexible member suitable for tissue fixation in the body.

The term "luggage tag stitch" is defined as any cinch or loop that is formed by the luggage tag technique.

What is claimed is:

1. A method of tissue repair comprising:
    passing a flexible construct through or around tissue to be repaired;
    passing a tail of the flexible construct through a loop of the flexible construct to form a cinch; and
    forming a locking mechanism adjacent the cinch to prevent passage of the tail back through the loop,
    wherein forming the locking mechanism includes applying a mechanical compression force on the flexible construct so that a core forms a bulge that protrudes outward of a braid of the flexible construct and thereby creates an obstruction for preventing loosening of the flexible construct through the loop.

2. The method of claim 1, wherein the cinch is a racking hitch or a half hitch, and wherein the locking mechanism acts as a stopper.

3. The method of claim 1, wherein the flexible construct is a suturing construct and the loop is a flexible, continuous, self-locking, adjustable, tensionable suture loop.

4. The method of claim 3, wherein the flexible construct consists essentially of suture.

5. The method of claim 3, wherein the bulge includes a width greater than a width of the flexible construct.

6. The method of claim 3, wherein the core is a monofilament core.

7. The method of claim 3, wherein the suturing construct is formed of suture, silk, cotton, nylon, polypropylene, polyethylene, ultrahigh molecular weight polyethylene (UHMWPE), polyethylene terephthalate (PET), polyesters or copolymers, or combinations thereof.

8. The method of claim 1, wherein the braid is formed of ultrahigh molecular weight polyethylene (UHMWPE).

9. The method of claim 1, wherein the flexible construct is a cerclage construct and the loop is a cerclage loop.

10. The method of claim 9, wherein the flexible construct consists essentially of cerclage tape.

11. The method of claim 1, wherein the mechanical compression force forms a crimped area in the flexible construct.

12. The method of claim 11, wherein the crimped area allows the core to protrude outward of the braid and thereby form the bulge.

13. The method of claim 1, wherein the loop is part of the core.

14. The method of claim 1, wherein the loop is part of the braid.

15. The method of claim 1, wherein the loop is part of both the core and the braid.

16. The method of claim 1, wherein the flexible construct excludes any knots.

17. A method of tissue repair comprising:
    passing a flexible construct through or around tissue to be repaired;
    forming a racking hitch in the flexible construct;
    passing a tail of the flexible construct through the racking hitch;
    tensioning the tail to cinch the flexible construct around the tissue; and
    applying a mechanical pressure at a region of the flexible construct adjacent to the racking hitch to form a bulge that functions as a stopper for preventing the tail from sliding back through the racking hitch, wherein applying the mechanical pressure includes applying a compression force to the flexible construct to provide a crimped area that causes a core to protrude through and beyond an outer surface of a braid of the flexible construct and thereby form the bulge.

18. The method of claim 17, wherein the mechanical pressure is applied after tensioning the tail to cinch the flexible construct, and the bulge formed as a result of the mechanical pressure is positioned to obstruct reverse passage of the tail through the racking hitch.

19. The method of claim 17, wherein the core is a monofilament core of the flexible construct.

* * * * *